United States Patent
Burcher

(10) Patent No.: US 9,561,017 B2
(45) Date of Patent: Feb. 7, 2017

(54) COMBINED PHOTOACOUSTIC AND ULTRASOUND IMAGING SYSTEM

(75) Inventor: Michael Burcher, Tarrytown, NY (US)

(73) Assignee: Koninklijke Philips N.V., Eindhoven (NL)

( * ) Notice: Subject to any disclaimer, the term of this patent is extended or adjusted under 35 U.S.C. 154(b) by 945 days.

(21) Appl. No.: 12/520,157

(22) PCT Filed: Dec. 19, 2007

(86) PCT No.: PCT/IB2007/055231
§ 371 (c)(1),
(2), (4) Date: Jun. 19, 2009

(87) PCT Pub. No.: WO2008/075299
PCT Pub. Date: Jun. 26, 2008

(65) Prior Publication Data
US 2010/0049044 A1 Feb. 25, 2010

Related U.S. Application Data

(60) Provisional application No. 60/870,713, filed on Dec. 19, 2006.

(51) Int. Cl.
*A61B 8/00* (2006.01)
*A61B 8/14* (2006.01)
(Continued)

(52) U.S. Cl.
CPC .............. *A61B 8/14* (2013.01); *A61B 5/0035* (2013.01); *A61B 5/0059* (2013.01);
(Continued)

(58) Field of Classification Search
None
See application file for complete search history.

(56) References Cited

U.S. PATENT DOCUMENTS

| 7,593,558 B2 | 9/2009 | Boese |
| 2004/0030253 A1* | 2/2004 | Brock-Fisher et al. ...... 600/458 |

(Continued)

FOREIGN PATENT DOCUMENTS

| EP | 1493380 A1 | 1/2005 |
| EP | 1561424 A1 | 8/2005 |

OTHER PUBLICATIONS

Frenz, Martin et al "Combined Ultrasound and Optoacoustic System for Real-Time High-Contrast Vascular Imaging in Vivo" IEEE Transactions on Medical Imaging, vol. 24, No. 4, Apr. 1, 2005, pp. 436-440.

Simon, Claudio et al "Motion Compensation Algorithm for Non-Invasive Two-Dimensional Temperature Estimation using Diagnostic Pulse-Echo Ultrasound" Proc. of SPIE, vol. 3249, 1998, pp. 182-192.

(Continued)

*Primary Examiner* — Long V Le
*Assistant Examiner* — Bradley Impink

(57) ABSTRACT

The present disclosure provides for a system that is adapted to simultaneously display photoacoustic and ultrasound images of the same object. An image combiner can perform spatial and temporal interpolation of the two images before generating a combined image. The combined image is then displayed on a display such as an LCD or CRT. The system is able to use motion estimates obtained from the ultrasound data to enhance the photoacoustic image thereby increasing its apparent frame rate, registering consecutive frames in order to reduce artifacts. The system is capable of generating combined ultrasound and photoacoustic images which are registered spatially and temporally.

14 Claims, 2 Drawing Sheets

Figure 1A:
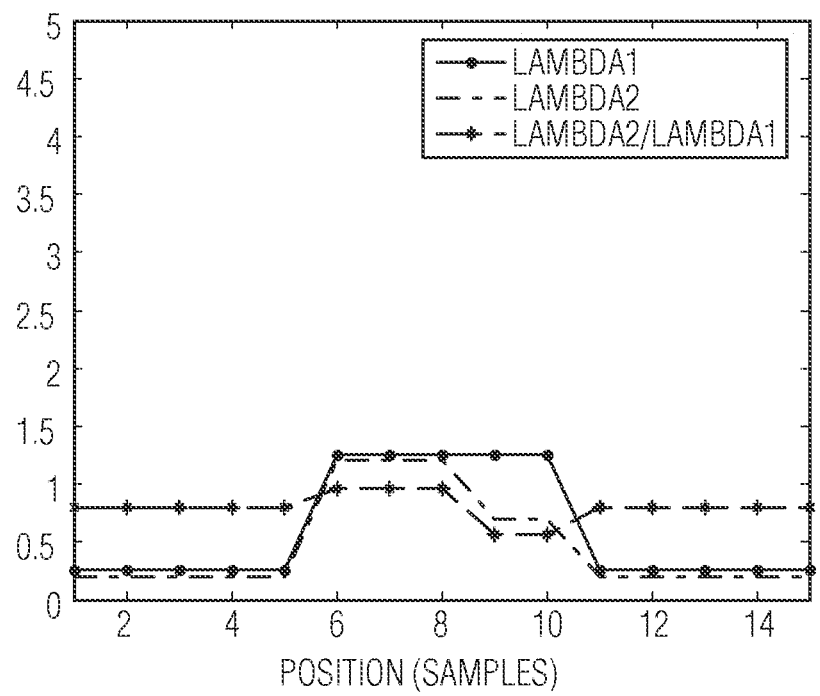

(51) Int. Cl.
  *A61B 5/00*   (2006.01)
  *G01N 21/17*  (2006.01)
  *G01S 7/52*   (2006.01)
  *G01S 15/89*  (2006.01)
  *A61B 8/08*   (2006.01)

(52) U.S. Cl.
  CPC .......... *A61B 5/0095* (2013.01); *A61B 5/7207* (2013.01); *A61B 8/4416* (2013.01); *A61B 8/5238* (2013.01); *A61B 8/5276* (2013.01); *G01N 21/1702* (2013.01); *G01S 7/52074* (2013.01); *G01S 15/899* (2013.01); *A61B 8/08* (2013.01); *A61B 8/488* (2013.01)

(56) References Cited

U.S. PATENT DOCUMENTS

| | | | |
|---|---|---|---|
| 2004/0067000 A1 | 4/2004 | Bates | |
| 2005/0085725 A1 | 4/2005 | Nagar | |
| 2005/0187471 A1* | 8/2005 | Kanayama et al. | 600/437 |
| 2014/0198606 A1* | 7/2014 | Morscher | A61B 5/0095 367/11 |
| 2014/0316244 A1* | 10/2014 | Abe | A61B 5/0095 600/409 |
| 2015/0359434 A1* | 12/2015 | Umezawa | A61B 5/7207 600/407 |

OTHER PUBLICATIONS

Manohar, Srirang et al "The Twente Photoacoustic Mammoscope: System overview and Performance" Physics in Medicine and Biology, vol. 50, 2005, pp. 2543-2557.

Wang, X. et al "Noninvasive Laser-Induced Photoacoustic Tomography for Structural and Functional in Vivo Imaging of the Brain" Nature Biotechnology, vol. 21, No. 7, pp. 803-806. Jul. 2003.

O'Donnell, Matthew et al "Internal Displacement and Strain Imaging using Ultrasonic Speckle Tracking" IEEE Trans. on Ultrasonics, Ferroelectrics and Frequency Control, vol. 41, No. 3, May 1994. pp. 314-325.

Xu, Minghua et al "Universal Back-Projection Algorithm for Photoacoustic Computed Tomography" Physical Review E, vol. 71, No. 1, pp. 16705 (2005).

Konogagou, Elisa E. et al "Shear Strain Estimation and Lesion Mobility Assessment in Elastography", Ultrasonics, Vol. 38, No. 108, pp. 400-404, 2000.

Thevenaz, Philippe et al "Interpolation Revisited" IEEE Transactions on Medical Imaging, vol. 19, No. 7, Jul. 2000, pp. 739-758.

Niederhauser, Joel J. et al "Combined Ultrasound and Optoacoustic System for Real-Time High-Contrast Vascular Imaging in Vivo" IEEE Trans. on Medical Imaging, vol. 24, No. 4, Apr. 2005, pp. 436-440.

Chen, E.J. et al "Ultrasound Tissue Displacement Imaging with Application to Breast Cancer" Ultrasound in Med. and Biology, vol. 21, No. 9, pp. 1153-1162, 1995.

Karim, Hezerul A. et al "Low Rate Video Frame Interpolation—Challenges and Solution" Proc. Acoustics, Speech and Signal Processing, 2003, vol. 3, p. III-117-120.

* cited by examiner

COMBINED PHOTOACOUSTIC AND ULTRASOUND IMAGING SYSTEM

The present disclosure relates to systems and methods related to photoacoustic and ultrasound imaging.

Photoacoustic (PA) tomography is an emerging medical imaging modality. (See, e.g., S. Manohar, A. Kharine, J. C. G. van Hespen, W. Steenbergen, and T. G. van Leeuwen, "The Twente Photoacoustic Mammoscope: System Overview and Performance," Physics in Medicine and Biology, Vol. 50, No. 11, pp. 2543-2557, June 2005; M. Xu and L. Wang, "Universal back-projection algorithm for photoacoustic computer tomography," Physical Review E, Vol. 71, No. 1, pp. 16706, 2005.) Typically, a short laser pulse is fired at an object of interest (for example, human or animal tissue). Laser energy is absorbed by structures within the object, causing a rapid temperature increase and thermal expansion. This thermal expansion causes ultrasound waves to propagate through the object, where they are received by ultrasound transducers positioned on the surface of the object. These signals can be beamformed in order to produce an image of the object's absorption at the wavelength of the laser. Since the laser radiation is scattered within the object, the illumination is not strongly focused, and an image can be formed from a single laser pulse. In order to increase the signal to noise ratio (SNR), several of these images may be averaged.

Ultrasound imaging is an established medical imaging modality. Images are formed by transmitting focused pulses of ultrasound energy into the body. The pulses are reflected by boundaries between structures within the body. The reflections propagate back to the ultrasound transducer and are then beamformed to create one A-line. Each transmission is used to form one line of the ultrasound image. An ultrasound image is therefore formed by multiple transmissions.

Recently, there has been an interest in performing photoacoustic imaging combined with ultrasound imaging. (J. Niederhauser, M. Jaeger, R. Lemor, P. Weber, and M. Frenz, "Combined Ultrasound and Optoacoustic System for Real-Time High-Contrast Vascular Imaging In Vivo," IEEE Transactions on Medical Imaging, Vol. 24, No. 4, pp. 436-440, April 2005.) So far, these systems have operated in two modes: producing either photoacoustic or ultrasound images, depending on the selected mode, even though much of the hardware and processing is common to both types of imaging.

Researchers have described systems where the images from the two modalities are displayed side-by-side. (See, e.g., J. Niederhauser, M. Jaeger, R. Lemor, P. Weber, and M. Frenz, "Combined Ultrasound and Optoacoustic System for Real-Time High-Contrast Vascular Imaging in Vivo," IEEE Transactions on Medical Imaging, vol. 24, no. 4, pp. 436-440, April 2005.) The problem with this arrangement is that it can be hard to identify features in the two images which originate from the same anatomical structure.

The frame rate of the PA image is limited by the pulse repetition rate of the laser and the (possible) need to average several pulses to achieve a sufficient signal-to-noise ratio. The pulse repetition rate for a typical laser is 10 Hz. This is therefore the maximum frame rate of the PA images. Averaging will reduce it. This is a significantly lower rate than the ultrasound frame rates are typically 60 Hz for an imaging depth of 10 cm and 128 image lines. If the PA images and ultrasound images are acquired in an interleaved fashion, then the rates may be reduced accordingly. For example, if PA images are acquired at 10 Hz, then the ultrasound frame rate would be reduced by 5 Hz to 55 Hz.

The relatively low frame rate of PA images can make combining different PA frames difficult. This needs to occur when several PA frames are averaged, or PA frames acquired with different wavelengths are compared. (See, e.g., X. Wang, Y. Pang, G. Ku, X. Xie, G. Stoica, and L. Wang, "Noninvasive laser-induced photoacoustic tomography for structural and functional in vivo imaging of the brain," Nature Biotechnology, Vol. 21, No. 7, pp. 803-806, July 2003.) The object being imaged (for example, the human body or a small animal) may move between the times when the two frames are acquired. If the frames are being averaged, this will reduce the spatial resolution of the resulting image. If the frames correspond to different laser wavelengths, then the motion will cause misregistration and possibly artifacts, as shown in FIG. 1 (b).

Figure 1B:
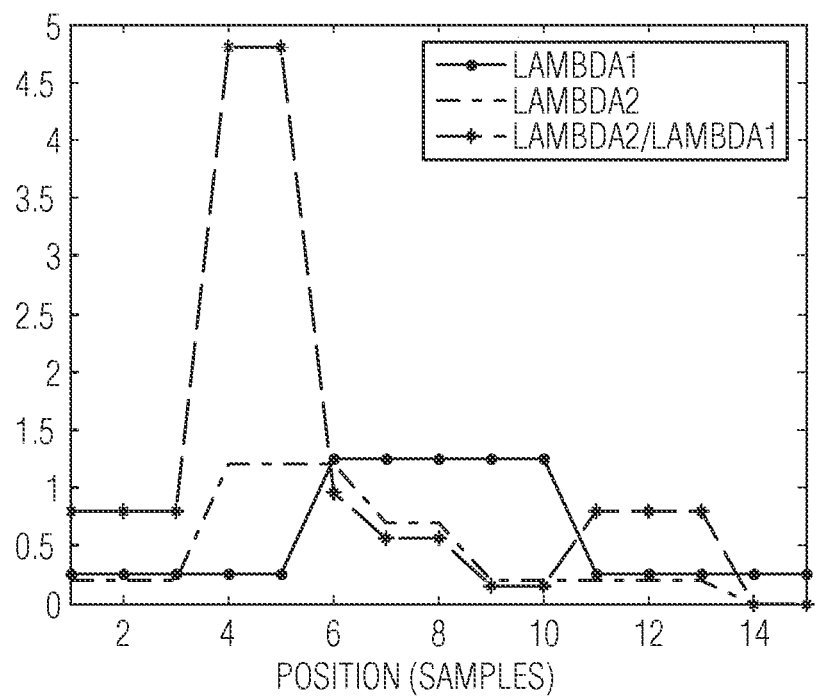

Referring to FIGS. 1(a) and 1(b), artifacts resulting from incorrect registration of PA frames acquired with different wavelengths (lambda 1 and lambda 2) are displayed. The graphs represent a cross-section through an image. The abscissa is the pixel value. In FIG. 1(a), the two frames are correctly registered. The correct ratio between the images at the two wavelengths is shown in black. In FIG. 1 (b), the lambda 2 frame has been shifted due to motion during the time between frames. The ratio is now incorrect and shows a large artifactual value at the 4th and 5th samples.

Accordingly, a need exists for an effective image combining system for PA and ultrasound images. These and other needs are addressed and/or overcome by the assemblies and methods of the present disclosure.

The present disclosure provides systems and methods for generating photoacoustic images and ultrasound images in real time. An exemplary imaging system associated with the present disclosure includes: (a) a means for generating photoacoustic signals; (b) at least a first transducer adapted to: (i) transmit ultrasound waves; (ii) receive ultrasound signals generated from the ultrasound waves; and (iii) receive photoacoustic signals generated from the photoacoustic signal means; (c) a motion estimator adapted to estimate motion based on the ultrasound signals; and (d) an image combiner adapted to receive and combine ultrasound data, photoacoustic data and motion estimator data generated from the received ultrasound and photoacoustic signals and the motion estimator and correct for motion to generate at least a photoacoustic image. The photoacoustic image may be corrected for motion by the image combiner using the motion estimator data. An exemplary image combiner is adapted to receive and combine ultrasound data, photoacoustic data and motion estimator data generated from the received ultrasound and photoacoustic signals and the motion estimator to generate a combined image.

In an exemplary system according to the present disclosure, combined images are received by a frame buffer adapted: (i) to store combined image output generated from the image combiner, and (ii) transmit the combined image to a display means. Typically, the photoacoustic signal means is accomplished by an illumination system adapted to generate a photoacoustic signal within a sample. Generally, the illumination system is characterized by an energy beam, such as a laser. The display means can be any display system, typically used for medical imaging such as an LCD or a CRT.

In an exemplary embodiment, the frame buffer is adapted to transmit a series of combined images at a rate of about 55 Hz. Typically, the received ultrasound signals are beamformed by an ultrasound beamformer to create a series of radio frequency signals. A portion of the radio frequency signals are received by the motion estimator and the remaining portion are detected and pass through an ultrasound scan converter to generate an ultrasound image adapted to be received by the image combiner. In an exemplary embodiment, all the radio frequency signals are received by the motion estimator when generating only PA images to correct for motion distortion in the PA imaging. Generally, the ultrasound signal pathway includes passing through a series of stages including filtering, detection and compounding. The motion estimator is adapted to generate a compensation signal to be received by the image combiner. An exemplary image combiner associated with the present disclosure is adapted to receive ultrasound image signals at a rate of about 55 Hz.

In an exemplary embodiment, the received photoacoustic signals pass through a photoacoustic scan converter adapted to generate a photoacoustic image to be received by the image combiner. An exemplary image combiner according to the present disclosure is adapted to receive photoacoustic image signals at a rate of about 10 Hz. Typically, the motion estimator is adapted to estimate motion of an object based on the portion of radio frequency signals. In an exemplary embodiment, ultrasound signals can be generated in a pulsed Doppler mode.

An exemplary image combiner according to the present disclosure is adapted to generate a sequence of combined frames containing data resulting from the received ultrasound signals and data resulting from the received photoacoustic signals. The sequence of combined frames is transmitted to a frame buffer. The image combiner should be adapted to perform spatial and temporal interpolation and resampling of the received photoacoustic signals. Typically, the image combiner is adapted to generate an output frame based on a combination of pixel values of at least one ultrasound image and at least one photoacoustic image.

In an exemplary embodiment, the display means is adapted to allow different images to be spatially registered, such that corresponding anatomical features in each image can be identified. The display means is adapted to display images in a displaying option selected from the group consisting of: displaying photoacoustic images only, displaying photoacoustic images and ultra sound images next to one another, overlaying a photoacoustic image on to an ultrasound image, using Doppler information to select which photoacoustic pixels are displayed, and combining Doppler and photoacoustic oxygenation information.

The present disclosure describes an exemplary method of combining images of a sample including: (a) illuminating a sample with an illumination system adapted to generate photoacoustic signals; (b) transmitting ultrasound waves to the sample with an ultrasound transmitting means adapted to receive ultrasound signals and photoacoustic signals; (c) generating ultrasound images from a portion of the received ultrasound signals via an ultrasound imaging means; (d) generating a motion estimation from a remaining portion of the received ultrasound signals via a motion estimator; (e) generating photoacoustic images from the received photoacoustic signals via a photoacoustic imaging means; and (f) combining the ultrasound images, the motion estimation and the photoacoustic images in an image combiner adapted to transmit the combined image to a display means.

Additional features, functions and benefits of the disclosed systems and methods will be apparent from the description which follows, particularly when read in conjunction with the appended figures.

Figure 2:
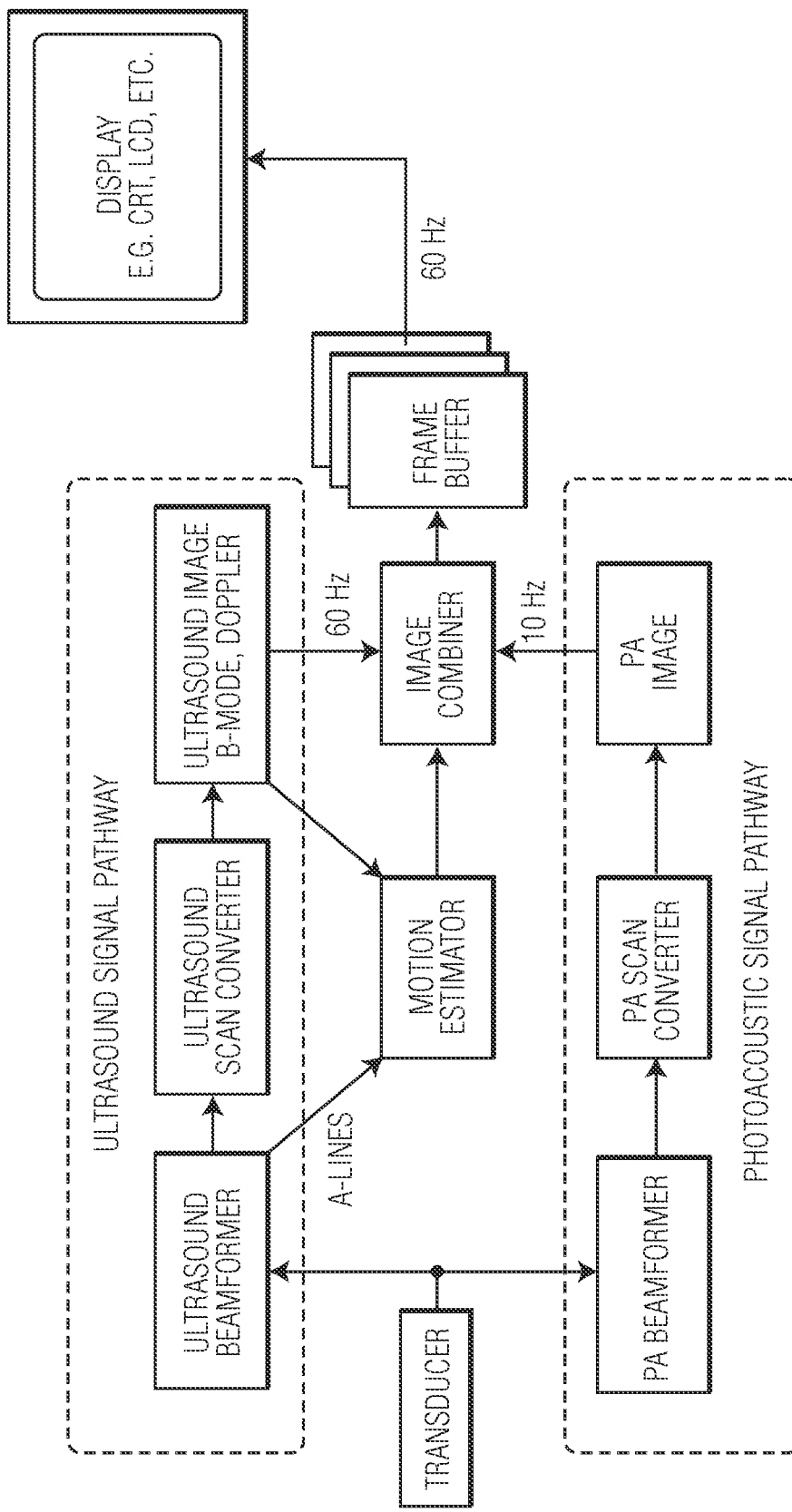

To assist those of ordinary skill in the art in making and using the disclosed systems and methods, reference is made to the appended figures, wherein:

FIG. 1(a) and FIG. (1b) are graphs illustrating artifacts resulting from incorrect registration of PA frames acquired with different wavelengths;

FIG. 2 is a schematic illustrating a combined PA and ultrasound imager system associated with the present disclosure.

The present disclosure relates to systems and methods that combine photoacoustic (PA) and ultrasound images. Such systems and methods are capable of generating images using PA or ultrasound image generating means. The acquisition of these images can be interleaved so that, from the point-of-view of the user, they appear to be acquired simultaneously. The two imaging modalities rely on different contrast mechanisms, and they will therefore generate different information. For example, an ultrasound image shows boundaries between different tissues with different acoustic impedances, whereas a PA image shows absorption of laser energy at the associated optical wavelength used.

Systems according to the present disclosure are used to simultaneously display PA and ultrasound images of the same object. An exemplary embodiment of a system associated with the present disclosure includes an image combiner that performs spatial and temporal interpolation of two images (PA and ultrasound) before generating a combined image. The combined image is then displayed on a display means such as a CRT and/or an LCD. In an exemplary embodiment the combined image can also be transmitted as data to a data storage or processing means such as a printer, a hard disk, a compact disk, and/or a flash drive. An exemplary image combiner according to the present disclosure is able to use motion estimates obtained from ultrasound data to enhance a photoacoustic image: increasing its apparent frame rate, registering consecutive frames in order to reduce artifacts. An exemplary combined system may be capable of generating combined ultrasound and PA images that are registered spatially and temporally.

Referring to FIG. 2, a schematic of an exemplary image combiner for a combined PA and ultrasound imaging system is shown. An exemplary system according to the present disclosure is used in conjunction with an ultrasound signal pathway, a PA signal pathway, a motion estimator, a frame buffer and a display. Ultrasound images are typically formed using a transducer, ultrasound beamformer and an ultrasound scan converter. These components may be the same as those typically found in an existing modem ultrasound machine. Ultrasound energy is transmitted in a series of focused beams using an ultrasound beamformer and a transducer. The energy received by the transducer is then beamformed to create a corresponding series of radio frequency (RF) signals, known as A-lines. These signals are detected and then scan converted to form a B-mode ultrasound image. The same components can also be used in a pulsed Doppler mode to detect and measure motion.

PA signals are generated by illuminating an object with a short laser pulse. The signals are received by a transducer that is common to PA and ultrasound signal pathways. The signals pass through a PA beamformer, which allows them to be spatially localized. The PA scan converter is then used to resample the signals and produce a PA image. In an exemplary embodiment, a single transducer is deployed to transmit ultrasound waves, receive ultrasound signals generated by the transmitted ultrasound waves and receive PA signals. However, systems associated with the present disclosure also include embodiments having multiple transducers. In an exemplary embodiment, a first transducer transmits ultrasound waves and a second transducer receives ultrasound signals generated by the transmitted ultrasound waves and receives the PA signals.

A motion estimator is used to estimate the motion of the object using the ultrasound data. To accomplish motion estimation, it is necessary to compare the signals received at different times from the same image location. This can be done using the RF A-line signals before they are detected and scan converted. Accordingly, it is possible to estimate the axial motion very accurately. Such motion estimation methods have previously been used in elastography. (See, e.g., E. E. Konofagou, T. Harrigan, and J. Ophir, "Shear strain estimation and lesion mobility assessment in elastography," Ultrasonics, Vol. 38, No. 1-8, pp. 400-4, 2000; J. Ophir, S. K. Alam, B. Garra, F. Kallel, E. Konofagou, T. Krouskop, and T. Varghese, "Elastography: ultrasonic estimation and imaging of the elastic properties of tissues," Proceedings of the Institution of Mechanical Engineers. Part H, Journal of Engineering in Medicine, Vol. 213, No. 3, pp. 203-33, 1999; J. Ophir, I. Cespedes, H. Ponnekanti, Y. Yazdi, and X. Li, "Elastography: a quantitative method for imaging the elasticity of biological tissues," Ultrasonic Imaging, Vol. 13, No. 2, pp. 111-34, 1991.) The contents of the foregoing publications are incorporated herein by reference.

It is also possible to estimate the motion from a series of ultrasound images (after detection and scan conversion) using speckle tracking. (See, e.g., E. J. Chen, R. S. Adler, P. L. Carson, W. K. Jenkins, and W. D. O'Brien, Jr., "Ultrasound tissue displacement imaging with application to breast cancer," Ultrasound in Medicine and Biology, Vol. 21, No. 9, pp. 1153-62, 1995; M. O'Donnell, A. R. Skovoroda, B. M. Shapo, and S. Y. Emelianov, "Internal displacement and strain imaging using ultrasonic speckle tracking," IEEE Transactions on Ultrasonics, Ferroelectrics and Frequency Control, Vol. 41, No. 3, pp. 314-25, May 1994.) In an exemplary embodiment, the motion estimator receives signals from the ultrasound beamformer and the ultrasound images to generate motion estimation.

A further alternative estimation method includes using Doppler information derived from specific Doppler sequences. (See, e.g., D. A. Christensen, *Ultrasonic Bioinstrumentation:* John Wiley & Sons, 1988.) The contents of the foregoing publications are incorporated herein by reference. It is understood that ultrasound image generators do not need to contain contrasting structures in order to perform motion estimation. The motion estimation can be performed on regions of uniform speckle texture.

Motion information extracted from the ultrasound signals may be displayed on the ultrasound image. Commercial ultrasound scanners typically include continuous wave Doppler, color Doppler, power Doppler and pulsed Doppler modes. Some also feature elastography, Doppler strain rate imaging and tissue Doppler imaging.

An exemplary image combiner according to the present disclosure may perform at least the following two functions:

1. Spatial and temporal interpolation and resampling of a PA image sequence, thus making use of the motion estimates derived from the ultrasound signals; and 2. Generating an output frame based on a combination of the pixel values in one of more ultrasound images and one or more PA images.

The output of the image combiner is typically a sequence of combined frames containing both ultrasound and PA information. This information is typically stored in a frame buffer. The frame buffer includes a plurality of frames adapted to be sequentially displayed on a display means. Exemplary display means include but are not limited to a CRT, LCD, or any other type of information display system.

Systems according to the present disclosure are adapted to allow for images acquired by ultrasound and PA modalities to be displayed on a single displaying means. Moreover, exemplary systems allow these images to be displayed at the same rate, even though they are acquired at different rates. Exemplary systems allow for different images to be spatially registered, such that corresponding anatomical features in the two images can be identified. Further aspects associated with the present disclosure include allowing for different PA images to be registered before being combined, thus reducing misregistration artifacts.

Spatial and temporal resampling of a PA image sequence functions as follows:

1. Spatial Resampling:

A PA image may be reconstructed on a different spatial grid from an ultrasound image. Spatial interpolation and resampling of a PA image is therefore required before it can be overlaid on an ultrasound image. This functionality may be performed within a PA scan conversion module. However, it may be desirable to perform certain operations, such as combining multiple PA frames, before spatial resampling (for increased accuracy, or less computation). (See, e.g., P. Thevenaz, T. Blu, and M. Unser, "Interpolation revisited [medical images application]," *Medical Imaging, IEEE Transactions,* Vol. 19, No. 7, pp. 739-758, 2000.)

2. Temporal Up-Sampling without Ultrasound:

PA frames can be temporally up-sampled using standard techniques developed for video. (See, e.g., H. A. Karim, M. Bister, and M. U. Siddiqi, "Low rate video frame interpolation—challenges and solution," in Proc. Acoustics, Speech, and Signal Processing, 2003. Proceedings. (ICASSP '03), 2003 IEEE International Conference on, 2003, Vol. 3, pp. III-117-20 vol. 3.) This allows a PA frame to be interpolated for each ultrasound frame. Alternatively, both PA frames and ultrasound frames can be interpolated to a video display rate.

3. Using Ultrasound Motion Information to Increase Perceived PA Refresh Rate:

Typical a maximum frame rate for an exemplary PA imaging system is about 10 Hz. An image that is refreshed at this rate, will appear to be "jerky" to a user. Using an exemplary system associated with the present disclosure, the motion and deformation of objects within the image can be detected and estimated by a motion estimator. The ultrasound motion field (which is typically measured at 55 Hz) can then be used to warp the PA image. The warped PA image can then be displayed at a 65 Hz rate.

4. Using Ultrasound Motion Information to Register PA Images Before Combining:

As mentioned above, combining two PA frames that are not properly registered can lead to blurring or other artifacts. The ultrasound motion field can be used to estimate the deformation of an object that occurred during the interval between the PA frame acquisitions. The motion field can then be used to warp one of the PA frames, such that both frames correspond to the same configuration of the object. This will reduce the blurring and artifacts.

5.Using Ultrasound Motion Information to Decide Which Parts of PA Images to Combine:

It is possible that some structures within a field-of-view of a particular PA image will be moving too fast to be tracked accurately by an ultrasound motion estimator. This fast motion may still be indicated by the motion estimator. For example, the correlation values in a speckle tracking algorithm may be below a certain threshold. Rather than trying to register these parts of an image by warping, it may be advantageous to not combine these parts of the PA frames.

6. Using Ultrasound Information to Detect when a Large Change in Probe Position has Occurred and Stop Averaging:

As mentioned above, it may be necessary to average several PA frames in order to achieve sufficient signal-to-noise ratio (SNR). This decreases the temporal resolution of an exemplary system and gives persistence to the image. This has a disadvantage in that, when a probe is moved to a different part of the body, or a different orientation, the previous image will persist, even though it corresponds to very different anatomy. The ultrasound can be used to detect this condition and reset the averaging, such that the previous image is not overlaid on a new image. In this scenario, it may also be appropriate to stop the display of the PA image for a few frames until enough (registered) images are available to average and produce a good image with sufficient SNR.

A combined imaging system according to the present disclosure can be adapted to accomplish several displaying options including but not limited to:

1. Displaying PA Image Only:

A PA image can still be enhanced by ultrasound motion information as described above.

2. Displaying PA and Ultrasound Images Next to One Another

Images are displayed at the same (video) rate, even though they are acquired at different rates.

3. Overlaying a PA Image on to an Ultrasound Image:

PA images can be displayed using a different color-map then that used to display ultrasound images. The PA image can be set at a threshold such that pixels below the threshold appear transparent and the user can "see through" to the ultrasound image behind. The roles of the images can be reversed so that the ultrasound image is overlaid on the PA image.

4. Using Doppler Information to Select which PA Pixels are Displayed:

Doppler signals from the ultrasound (color Doppler, or power Doppler) can be used to detect where there is motion within an image scan. PA images will only be displayed as a color overlay on pixels where the Doppler signal exceeded a certain threshold setting. Blood, for example, is a strong absorber for wavelengths of light normally used for PA imaging. The resulting image would thus be an image of blood moving above a certain speed.

5. Combining Doppler and PA Oxygenation Information:

By comparing PA images at two different wavelengths, it is possible to determine the oxygenation of blood. The oxygenation value can be multiplied by the velocity derived from the Doppler signal, and the result displayed as an image to a user. The image would be a measure of the rate at which oxygen was being transported in the blood vessels being imaged.

Examples of possible uses for an exemplary system associated with the present disclosure include but are not limited to medical imaging of humans, or small animals. An exemplary imaging system can be added to an existing modem ultrasound machine, such as, for example, a Philips iU22 or iE33.

Although the present disclosure has been described with reference to exemplary embodiments and implementations thereof, the disclosed systems and methods are not limited to such exemplary embodiments/implementations. Rather, as will be readily apparent to persons skilled in the art from the description provided herein, the disclosed systems and methods are susceptible to modifications, alterations and enhancements without departing from the spirit or scope of the present disclosure. Accordingly, the present disclosure expressly encompasses such modification, alterations and enhancements within the scope hereof.

The invention claimed is:

1. A combined photoacoustic and ultrasound imaging system, comprising:
   (a) a laser configured to illuminate an object and thereby generate photoacoustic signals emitted from the object;
   (b) a transducer configured to:(i) transmit ultrasound waves to the object; (ii) receive ultrasound echo signals based on echoes reflected from the object in response to the transmitted ultrasound waves; and (iii) receive the photoacoustic signals generated from the laser illumination;
   (c) an ultrasound echo signal pathway coupled to the transducer to receive the emitted ultrasound echo signals and configured to produce ultrasound image data;
   (d) a photoacoustic signal pathway coupled to the transducer to receive the photoacoustic signals and configured to produce photoacoustic image data;
   (e) a motion processor coupled to the transducer to receive ultrasound echo signals reflected at different times from a same location on the object and configured to produce motion estimator data based on the ultrasound echo signals received at the different times from the same location; and
   (f) an image processor coupled to the photoacoustic signal pathway to receive the photoacoustic image data and coupled to the motion processor to receive the motion estimator data, wherein the image processor is configured to temporally correct the photoacoustic image data for motion based on the motion estimator data.

2. The system according to claim 1, comprising a frame buffer coupled to the image processor and a display, wherein the image processor is further coupled to the ultrasound echo signal pathway to receive the ultrasound image data and configured to produce combined images comprising ultrasound image data and photoacoustic image data; and
   wherein the frame buffer is configured to:
   (i) store the combined images; and
   (ii) transmit the combined images to the display for displaying the combined images.

3. The system according to claim 2, wherein the display is selected from the group consisting of a liquid crystal display (LCD) and a cathode ray tube (CRT).

4. The system according to claim 2, wherein the frame buffer is adapted to transmit the combined images at a rate of about 55 Hz.

5. The system according to claim 2, further comprising a beamformer in the ultrasound signal pathway and configured to beamform the ultrasound echo signals to create a series of radio frequency signals.

6. The system according to claim 5, wherein at least a portion of the radio frequency signals are received by the motion processor and the remaining portion pass through an ultrasound scan converter to generate ultrasound image data adapted to be received by the image processor.

7. The system according to claim 6, wherein the image processor is adapted to receive the ultrasound image data at a rate of about 55 Hz.

8. The system according to claim 2, further comprising a photoacoustic scan converter in the photoacoustic signal pathway and configured to to generate the photoacoustic image data adapted to be received by the image processor.

9. The system according to claim 8, wherein the image processor is adapted to receive the photoacoustic image data at a rate of about 10 Hz.

10. The system according to claim 2, wherein the display is configured to display images from the frame buffer based on a displaying option selected from the group consisting of: displaying motion corrected photoacoustic images only, displaying motion corrected photoacoustic images and ultrasound images next to one another, and overlaying a motion corrected photoacoustic image on to an ultrasound image.

11. The system according to claim 1, wherein the laser is configured to produce an energy beam directed at the object to produce the photoacoustic signals within the object.

12. The system according to claim 1, wherein the image processor is further configured to perform spatial and/or temporal interpolation and resampling of the photoacoustic image data using the motion estimator data.

13. The system according to claim 12, wherein the image processor is coupled to the ultrasound signal pathway to receive the ultrasound image data and is configured to generate an output frame from a combination of pixel values of the ultrasound image data and the photoacoustic image data.

14. A method of combined imaging of a sample comprising:
 (a) illuminating a sample with an illumination system thereby generating photoacoustic signals emitted from the sample;
 (b) transmitting ultrasound waves to the sample with an ultrasound transducer;
 (c) receiving with the ultrasound transducer ultrasound echo signals based on echoes reflected from the sample and the emitted photoacoustic signals from the sample;
 (d) generating a motion estimation from the ultrasound echo signals with at least two of the ultrasound echo signals being received at different times from a same location of the sample;
 (e) generating at least one photoacoustic image from the received photoacoustic signals; and
 (f) correcting the photoacoustic image for motion using the motion estimation from the ultrasound echo signals.

\* \* \* \* \*